(12) United States Patent
Tedder et al.

(10) Patent No.: US 7,393,933 B1
(45) Date of Patent: Jul. 1, 2008

(54) HEPATITIS B MONOCLONAL ANTIBODIES

(76) Inventors: Richard Seton Tedder, Department of Virology, UCL Medical School, Windeyer Building, 46 Cleveland Street, London W1P 6DB (GB); Samreen Ijaz, Department of Virology, UCL Medical School, Windeyer Building, 46 Cleveland Street, London W1P 6DB (GB); Ruth Bridget Ferns, Department of Virology, UCL Medical School, Windeyer Building, 46 Cleveland Street, London W1P 6DB (GB)

( * ) Notice: Subject to any disclaimer, the term of this patent is extended or adjusted under 35 U.S.C. 154(b) by 0 days.

(21) Appl. No.: 09/402,282

(22) PCT Filed: Apr. 25, 1997

(86) PCT No.: PCT/GB97/01161

§ 371 (c)(1),
(2), (4) Date: Apr. 24, 2000

(87) PCT Pub. No.: WO97/40164

PCT Pub. Date: Oct. 30, 1997

(30) Foreign Application Priority Data

Apr. 25, 1996 (GB) ................................. 9608626.9

(51) Int. Cl.
*C12P 21/08* (2006.01)
*C12K 16/00* (2006.01)
(52) U.S. Cl. .................................. 530/387.3; 530/388.8
(58) Field of Classification Search ............ 530/388.15
See application file for complete search history.

(56) References Cited

FOREIGN PATENT DOCUMENTS

WO 94/21812 * 9/1994

OTHER PUBLICATIONS

Mangold CM et al. "Secretion and antigenicity of hepatitis B virus small envelope proteins lacking cysteines in the major antigenic region". Virology. Aug. 20, 1995; 211(2):535-43.*

* cited by examiner

*Primary Examiner*—Bruce R. Campell
*Assistant Examiner*—Bo Peng
(74) *Attorney, Agent, or Firm*—Cheryl L. Becker; Audrey L. Bartnicki

(57) ABSTRACT

A monoclonal antibody that is capable of binding specifically to wild type HBsAg and to at least two mutant forms of HBsAg may be used in an improved immunoassay for the detection of both escape mutants and wild type HBsAg and may be used for passive immunisation against HBV.

6 Claims, 2 Drawing Sheets

FIGURE 1a

```
                                                     codon
                                                      122                                thr
                                                                                         asn
                                              gln              ilethr
1)
2)   leuleuproglyserserthrthrserthrglyprocyscysthrcysargthrcysthrthrproalaglnglylyilesermetpheproser
3)   ctaattccaggatcatcaaccaccagcacgggacacgggaccctgcagaacctgcacgactcctgctcaaggaatctctatgtatccctcc
4)        c                a ca       a  t          g a   cag       t t a              c a    a t
                             t        t                               t                  c    a t
5)                          t         gt             a                                   c    ca
6)                          t         a          ta                   t                  c    tc codon codon                                      codon
                         143   145                                         160
                                                                     alaarg
2)   cyscyscyscysthrlyspropseraspglyasncysthrcysileproileproserserlrpalapheglylyspheleutrpleu
3)   tgttgctgtacaaaccttcggatgaaactgcaccctgtattcccatcatcctggctttcggaaaattcctatgggag
4)        c           a   c       t        t                    g           c g   a
5)      c agt     t       aa      t                                             cg
6)        c           tc          t                              c         t FIGURE 1b
```

HEPATITIS B MONOCLONAL ANTIBODIES

This application is a 371 of PCT/GB97/01161 filed on Apr. 25, 1997, which claims priority under 35 U.S.C. Section 119(a) to GB Application Number 9608626.9, filed on Apr. 25, 1996.

On a global scale, the hepatitis B virus (HBV) is the most significant of the hepatotrophic viruses in terms of the number of people chronically infected and the severity of the complications of infection.

Hepatitis B emerged as a major problem after the introduction of parenteral therapy, mass immunisation campaigns and the extensive transfusion of blood and pooled blood products. Long incubation periods, high incidence of asymptomatic infections and the occurrences of an infectious carrier state make HBV well suited to transmission by blood. Numerous workers have also provided evidence for sexual transmission of HBV, and transmission of hepatitis B virus from carrier mothers to their babies can occur during the perinatal period.

HBV, a DNA virus, is a member of the hepadna virus group. Electron microscopy of the HBV reveals a double shelled, spherical particle of 42 nm in diameter called the "Dane particle". Those virus particles exhibit an electron dense spherical inner core with a diameter of approximately 22-25 nm and an outer coat 7 nm in thickness. The outer coat of the virus bears the surface antigen (called herein "HBs" or "HBsAg") to which virus-neutralizing antibody is directed. The spherical 20 nm diameter inner-core particles bear the viral core antigen (HBcAg) and the e antigen (HBeAg), the viral DNA, DNA polymerase activity and a protein kinase activity.

HBsAg contains the major neutralizing epitope of HBV, termed the "a" determinant, which spans amino acids 124 to 147 and is common to all HBV isolates, see for example, Pugh et al (1986). The development of anti-HBs after acute or chronic HBV infection is usually associated with recovery and a good prognosis. Anti-HBs is also associated with the production of neutralizing antibodies resulting from vaccination. The majority of anti-HBs found in convalescent and post-vaccination sera binds in the region of the "a" determinant, which has an as yet undefined structure. It is clear that the "a" determinant is highly conformational because denaturation of that area by alkylation or reduction gives rise to HBsAg particles with greatly reduced antigenicity. It is thought that disulphide bridges between cysteine residues are responsible for correct conformation. One possible structure of the "a" determinant involves a disulphide bridge between amino acids 124 and 137, forming a first loop, and a further disulphide bridge between amino acids 139 and 147, forming a second loop.

Anti-HBs is thought to bind predominantly to the second loop but it is thought that the epitopes are not confined to one loop only. The whole of the sequence of the "a" determinant probably contributes to the antigenic structure. The "a" determinant is conserved though there is a degree of amino acid variation in normal isolates of HBV. Greater variation is accepted in the first loop of the putative epitope, perhaps implying that this region does not contribute significantly to the neutralisation epitope.

The "a" determinant is found in all subtypes of HBV and it is variation of amino acids within and around the "a" determinant that gives rise to subtypes. HBsAg can be classified into four major immunological subtypes, adw, ayw, adr, and ayr, each with an associated geographical distribution. The d/y and w/r subtypes are determined by substitutions of lysine by arginine at amino acids 122 and 160 respectively.

Recently, the presence of HBsAg has been observed in anti-HBs serum samples of certain patients. The HBsAg in those patients may not be neutralised by the anti-HBs present, implying the presence of HBsAg variants. Significant variants (mutants) have been associated with vaccination, monoclonal antibody therapy, polyclonal antibody therapy and cases of HBV infection difficult to diagnose in clinical laboratories see, for example, Carmen et al. (1992, 1993), Harrison et al. (1993), Hawkins et al. (1994), Howard et al. (1993), McMahon et al. (1992), Okamoto et al. (1992), and Wallace et al. (1994).

Upon analysis the mutants seem to have been selected from a mixed population and to have point mutations causing amino acid substitutions in the "a" determinant. The mutants are thought to arise by random mutations within the gene which gives rise to a pool of genotypes. In the mutants described to date, it is thought that the immune response is the predominant factor in selecting for the mutants.

Generally, addition of monoclonal antibodies to virus infected cells in vitro result in selection of isolates that are not neutralised by that antibody. It is thus not surprising that monoclonal antibodies given to patients with active viral replication can result in selection of so-called "escape" mutants.

Several separate escape mutants with clinical significance have been described in vaccinated individuals. In three cases there was found to be a point mutation at the codon for amino acid 145 in the "a" determinant of HBsAg resulting in an amino acid change from glycine to arginine. Administration of serum containing one such mutant virus to a chimpanzee proved that the agents are transmissible.

In a mutant virus implicated in a breakthrough infection in a vaccinated population, a lysine to glutamic acid mutation at amino acid 141 of the "a" determinant was found. That and other point mutations resulting in one or more amino acid substitutions in the "a" determinant have since been reported in vaccinated individuals.

Escape mutants are a cause for concern on several accounts. Firstly, there is failure to detect such mutants by immunoassays. Diagnostic assays are designed to achieve high sensitivity and specificity. Assays for HBsAg detection depend on interaction between an anti-HBs reagent and HBsAg in the sample under investigation. A resulting anti-HBs/HBsAg complex is then detected. If there is a significant mutation in the HBsAg epitope and it is not recognised by the anti-HBs, then the HBsAg will either not be detected or the assay will be very insensitive. Failure to detect an escape mutant may not only affect the person harbouring the mutant; it may lead to transmission of infection through donated blood, blood products or organs. Secondly, HBV with mutant HBsAg may infect individuals even though they have been previously immunised and have an anti-HBs response.

A monoclonal antibody to an escape mutant at position 122 has been described in WO94/26904. That antibody is able to discriminate between the wild type HBsAg and the mutant form and hence enables identification of the mutant form.

The present invention provides a monoclonal antibody that is capable of binding specifically to wild-type HBsAg and to at least two, preferably more than two, mutant forms of HBsAg.

The ability of a monoclonal antibody of the present invention to bind specifically to both wild type and mutant HBsAg suggests that it is binding to a region of the surface antigen that is conserved between the wild type protein and the mutant forms. The conserved region and hence the antigenic determinant (or epitope) may be in the "a" determinant itself, in the region of the "a" determinant or even in a non-"a" region.

Because of its ability to bind specifically to mutant forms of HBsAg as well as to the wild type protein, and hence to detect escape mutants, a monoclonal antibody of the present invention is particularly useful in improving the efficacy of immunoassays for the detection of HBsAg, for clinical diagnosis of HBV infections and also for blood screening. The safety of the blood supply and of the supply of blood products may be improved by the use of a monoclonal antibody of the invention in an HBsAg assay, either alone, that is to say, as the only anti-HBs antibody or, especially, in addition to one or more other anti-HBs antibodies.

FIGS. 1a and 1b of the accompanying drawings set out amino acid and nucleic acid sequences of part of the HBV surface region encompassing the "a" determinant. FIG. 1b of the drawings as filed is a typescript version of FIG. 1a. In each of FIGS. 1a and 1b: Line 1 sets out recognized amino acid variants of subtype adyw (SEQ ID NO: 1); Line 2 sets out the consensus amino acid sequence of subtype adyw (SEQ ID NO:2); Line 3 sets out the consensus nucleic acid sequence of subtype adyw (SEQ ID NO:3); Line 4 sets out recognized nucleic acid variants (SEQ ID NO:4); Line 5 sets out the nucleic acid variants encoding Mutant HbsAg II (MAM HbsAg) (SEQ ID NO:5); and Line 6 sets out the nucleic acid variants encoding Mutant HbsAg I (NP HbsAg) (SEQ ID NO:6).

A further recognised nucleotide variant at position 143 is ACG for TCG, which results in threonine instead of serine at that position.

A putative monoclonal antibody of the present invention may be screened for the ability to bind specifically to three or more reference antigens namely wild type HBsAg and two or more mutant forms of HBsAg. A skilled worker is able readily to distinguish specific binding between an antibody and an antigen from non-specific binding. Any antibody that is capable of binding specifically to three or more such reference antigens is a monoclonal antibody of the present invention. Such a method of screening is itself part of the present invention. It should be noted that the term "binding" is used throughout the present specification to denote specific binding.

An HBsAg used for screening and/or as an antigen in the production of hybridomas and monoclonal antibodies of the invention may be a full length protein or may be an appropriate antigenic fragment or derivative of a wild type or mutant HBsAg.

A monoclonal antibody of the present invention may be of any immunoglobulin class, for example, IgG, IgM or IgA, and of any isotype.

Mutant forms of HBsAg may be found in mutant viruses having a mutation that leads to at least one amino acid substitution relative to wild type HBsAg, for example, as found in so-called "escape mutants". A mutant HBsAg may have a substitution in the "a" determinant or in the region of the "a" determinant, for example, the mutation may be a point mutation. A mutation, for example, a point mutation, may be within the sequence encoding amino acids 133 to 145 of HBsAg. The mutation may lead to an amino acid substitution at position 133 and/or at position 145. Further and/or different substitutions may be present, for example, at any one or more of positions 134, 141, 142, 143 and 144. A mutant HBsAg may, for example, have amino acid substitutions relative to the wild type at any one or more of positions 143, 144 and 145. Such mutations may be present in addition to other mutations, either in the "a" determinant or in another region.

A monoclonal antibody of the present invention is capable of binding specifically, for example, to wild-type HBsAg and to two or more different mutant HBsAg as described above, for example, each having a mutation at any one or more of positions 133, 134, 141, 142, 143, 144 and 145. Alternatively, binding may be to one mutant HBsAg described above and to a mutant HBsAg having a mutation in a different region.

Examples of mutant forms of HBsAg are those having the following substitutions relative to the wild type in the region of the "a" determinant:

Mutant HBsAG I ("NP" HBsAg): met to ile at amino acid 133; phe to his at amino acid 134; and asp to val at amino acid 144 (SEQ ID NO: 7);

Mutant HBsAg II ("MAM" HBsAg): met to ile at amino acid 133; phe to asn at amino acid 134; pro to ser at amino acid 142; ser to leu at amino acid 143; and gly to lys at amino acid 145 (SEQ ID NO: 8);

Mutant HBsAg III ("SZ" HBsAg): gly to arg at amino acid 145 (SEQ ID NO:9);

Mutant HBsAg IV ("SP" HBsAg): ser to met at amino acid 143 (SEQ ID NO:10).

A putative antibody may be screened, for example, against wild type HBsAg and against any two or more of the mutant forms described above. For example, a putative monoclonal antibody of the present invention may be screened against wild-type HBsAg and against two or more different mutant HBsAg each having mutation(s) at any one or more of positions 133, 134, 141, 142, 143, 144 and 145, especially 143, 144 and 145. Alternatively, one such mutant may be used with a mutant HBsAg having a mutation in a different region. Mutant forms I and IV described above may be used for screening.

The present invention provides a monoclonal antibody that is capable of binding specifically to wild-type HBsAg and to at least one mutant HBsAg carrying an "a" determinant coded for by a sequence having point mutations at any one or more of the codons encoding amino acids 143, 144 and 145. The monoclonal antibody may bind to two or more such mutant HBsAg or to one such mutant HBsAg and to another different mutant HBsAg.

Examples of monoclonal antibodies of the present invention are those produced by the hybridomas designated P2D3, M3A10 and M4F5, which hybridomas have been deposited at the European Collection of Cell Structures (ECACC), Virus Research and Production Laboratory, Public Health Laboratory Service, Centre for Applied Microbiology & Research, Porton Down, Salisbury, Wiltshire SP4 0JG, England, under the terms of the Budapest Treaty on the International Recognition of the Deposit of Microorganisms for the Purposes of Patent Procedure, 1977. The accession numbers and dates of the hybridoma deposits are as follows: Hybridoma P2D3: Accession Number ECACC 97042331, Accession Date 23 Apr. 1997; Hybridoma M3A10: Accession Number ECACC 97042330, Accession Date 23 Apr. 1997; Hybridoma M4F5: Accession Number ECACC 97042519, Accession Date 25 Apr. 1997.

In this specification, a monoclonal antibody may be referred to under the same designation as the hybridoma that produces it, for example, the monoclonal antibody designated P2D3 is as produced by hybridoma P2D3 (ECACC 97042331). Hybridomas P2D3 (ECACC 97042331), M3A10 (ECACC 97042330) and M4F5 (ECACC 97042519) and the monoclonal antibodies they produce are described in detail in the Examples below.

Each of the monoclonal antibodies P2D3, M3A10 and M4F5 is capable of binding specifically to (i) wild type HBsAG, (ii) Mutant HBsAG I (NP HBsAG) and (iii) Mutant HBsAg II (MAM HBsAg). Furthermore, each also is capable of binding specifically to Mutant HBsAg III (SZ HBsAg) and to Mutant HBsAg IV (SP HBsAg). Monoclonal antibodies P2D3 and M4F5 are IgG antibodies. Monoclonal antibody M3A10 is an IgA antibody.

It is known that wild type HBsAg has a number of different serotypes, and also that there are recognised mutants see, for example, Pugh et al 1980. The term "wild type HBsAg" as used in the present specification includes all HBsAg that are recognised in the art as wild type or that would be acknowledged to be wild type. The term therefore includes wild type HBsAg of all serotypes and of all recognised variants. The term "mutant HBsAg" as used herein does not include recognised wild type variants.

Suitable screening tests are well known to those skilled in the art and include cross-competition assays and assays, for example, using radio-labelled monoclonal antibody to determine binding specificities.

As stated above, the ability of a monoclonal antibody of the present invention to bind to both wild type and mutant HBsAg suggests that it is binding to a region of the surface antigen that is conserved between the wild type protein and the mutant forms. (See also the General Discussion below.) The location and the sequence of such a conserved region and hence a conserved epitope may be determined by known methods, for example, by epitope mapping optionally using a monoclonal antibody of the invention. Epitopic peptides and polypeptides may then be produced, for example, recombinantly, by chemical synthesis or by a combination of different methods. A resulting antigenic peptide or polypeptide may also be immunogenic. An epitope against which a monoclonal antibody of the invention is directed is itself part of the present invention.

The present invention includes fragments and derivatives of a monoclonal antibody of the present invention, for example, Fab and Fab$_2$ fragments and conjugates. Derivatives include humanized derivatives. Methods for producing fragments and derivatives, including humanized derivatives, are well known. For example, fragments and derivatives may be produced recombinantly. Fragments and derivatives of antibodies and their uses are well known to the skilled worker. The term "monoclonal antibody" as used herein includes fragments and derivatives thereof.

The present invention also provides an anti-idiotype antibody to a monoclonal antibody of the present invention. Such antibodies, which comprises an "internal image" of the original epitope, may be used as epitope substitutes and are particularly useful in the case of conformational epitopes, since it is difficult to map such epitopes and it may not be possible to produce synthetic epitopic peptides in such cases.

A monoclonal antibody of the present invention may be used in an immunoassay for the detection of HBsAg ("HBV assay") and hence of hepatitis B infections, either as a substitute for or, especially, in addition to anti-HBs antibodies currently used in HBV assays. Such assays may be used for clinical diagnosis or for blood screening, and the present invention includes both methods of diagnosis and methods of blood screening using an immunoassay comprising a monoclonal antibody of the present invention.

A monoclonal antibody of the present invention may also be used therapeutically or prophylactically as an antiserum for passive immunisation and/or to define an epitope for use as a vaccine in active immunisation. The present invention includes such antisera and methods of immunisation, and also epitopes defined using such antisera.

A further application of a monoclonal antibody of the present invention is in affinity chromatography, for example, to purify wild or mutant types of HBsAg, antigenic fragments thereof, antigenic peptides or anti-idiotype antibodies.

Accordingly, the present invention provides an immunoassay for the detection of HBsAg, which comprises contacting a sample under investigation with a monoclonal antibody of the present invention, a fragment or derivative thereof, or a combination of two or more thereof, and detecting any resulting antigen-antibody complex.

The term "detection" is used herein to denote detection and/or determination and includes qualitative, quantitative and semi-quantitative methods.

The monoclonal antibody of the invention, fragment, derivative or combination thereof may be used with one or more other antibodies selected from polyclonal anti-HBs antibodies and other monoclonal anti-HBs antibodies.

An immunoassay of the present invention may be in a homogeneous or heterogeneous format. The format may be a capture or a competitive format.

An immunoassay for the detection of antibodies to hepatitis B core antigen (anti-HBc) may be carried out simultaneously with the assay for HBsAg. HBV combination anticore/surface antigen assays are known and are in use.

The present invention further provides an immunoassay kit that comprises a monoclonal antibody of the present invention or a fragment or derivative thereof, or a combination of two or more thereof, and other reagents required for carrying out an immunoassay for HBsAg and optionally also reagents for detecting anti-HBc antibodies. One or more other anti-HBs antibodies selected from polyclonal anti-HBs antibodies and other monoclonal anti-HBs antibodies may be present, and the other reagents may be selected from washing solutions, diluents, standard solutions, control reagents and labelled anti-HBs antibodies.

The present invention further provides a solid phase suitable for use in an immunoassay on which is immobilised a monoclonal antibody of the present invention, a fragment or derivative thereof, or a combination of two or more thereof. One or more further anti-HBs antibodies selected from polyclonal anti-HBs antibodies and other monoclonal anti-HBs antibodies may also immobilised on the solid phase. Furthermore, an agent capable of capturing anti-HBc antibodies may be immobilised on the solid phase in addition to the anti-HBs antibodies.

The present invention further provides an antiserum suitable for use therapeutically or prophylactically for passive immunisation which comprises a monoclonal antibody of the present invention, a fragment or derivative thereof, or a combination of two or more thereof.

The present invention also provides a composition suitable for use therapeutically or prophylactically for passive immunisation against HBV which comprises a monoclonal antibody of the present invention, a fragment or derivative thereof, or a combination of two or more thereof, in admixture with a pharmaceutically suitable carrier.

An antiserum or composition of the invention may also comprises one or more other antibodies selected from polyclonal anti-HBs antibodies and other monoclonal anti-HBs antibodies.

The present invention further provides a method of therapeutic or prophylactic passive immunisation against HBV which comprises administering to a human a therapeutically or prophylactically effective amount of a monoclonal antibody of the invention, a fragment or derivative thereof or a combination of two or more thereof. One or more other antibodies selected from monoclonal and polyclonal anti-HBs antibodies may also be administered.

The present invention further provides isolated Mutant HBsAG I, Mutant HBsAG II, Mutant HBsAG III or Mutant HBsAG IV as defined above. The invention also provides a fragment or derivative of such a mutant HBsAg, said fragment or derivative being capable of binding specifically to a monoclonal antibody of the present invention or to a fragment or derivative thereof. A fragment or derivative of a mutant HBsAg may also be immunogenic. A mutant HBsAg or a fragment or derivative thereof is obtainable from a natural source or recombinantly. It may be preferable, for example, for use as an immunogen, to have the mutant HBsAg or fragment or derivative thereof in partially or fully glycosylated form. The present invention also provides a chemically synthesised antigenic and optionally also immunogenic epitopic peptide.

The present invention provides an vaccine composition that comprises a mutant HBsAg of the present invention or an immunogenic fragment or derivative thereof, or a combination of two or more thereof, and a pharmaceutically suitable carrier. A vaccine composition may further comprise one or more other immunogenic peptides or polypeptides, for example, other immunogenic HBsAg peptides or polypeptides.

The present invention also provides a method of vaccinating a human against HBV, which comprises administering to the human a therapeutically effective amount of a mutant HBsAg of the present invention, an immunogenic fragment or derivative thereof, or a combination of two or more thereof, optionally in combination with one or more other immunogenic HBsAg peptides or polypeptides.

The present invention also provides an isolated nucleic acid that encodes Mutant HBsAG I, Mutant HBsAG II, Mutant HBsAG III or Mutant HBsAG IV as defined above, or a fragment or derivative of such a mutant HBsAg, said fragment or derivative being capable of binding specifically to a monoclonal antibody of the present invention or to a fragment or derivative thereof. The fragment or derivative of the mutant HBsAg is preferably immunogenic.

The present invention also provides a composition that comprises a nucleic acid of the invention, especially a vaccine composition that comprises a nucleic acid of the invention in a form suitable for expression of the encoded amino acid sequence when administered to a mammal.

For any of the applications and uses according to the present invention, the monoclonal antibody of the present invention may be monoclonal antibody P2D3, monoclonal antibody M3A10, monoclonal antibody M4F5 or a combination of two of more thereof. Any one or more of the monoclonal antibodies P2D3, M3A10 and M4F5 may be used together with any other monoclonal antibody of the present invention and/or with any other anti-HBV antibodies, especially antiHBS antibodies. A fragment or derivative of a monoclonal antibody of the invention may be used.

The present invention also provides a hybridoma capable of producing a monoclonal antibody of the present invention, for example, hybridoma P2D3 (Accession Number ECACC 97042331), hybridoma M3A10 (Accession Number ECACC 97042330) and hybridoma M4F5 (Accession Number ECACC 97042519).

The present invention provides a method of producing a hybridoma capable of producing a monoclonal antibody of the present invention, which comprises immunizing an animal with wild type HBsAg or a mutant form of HBsAg, immortalizing antibody producing cells to form hybridomas, screening the resulting hybridoma culture against wild type HBsAg and two or more mutant forms of HBsAg, and selecting those hybridomas that produce a monoclonal antibody that is capable of binding specifically to wild type HBsAg and two or more mutant forms of HBsAg.

A monoclonal antibody of the invention may be obtained by culturing a hybridoma of the invention in vitro or in vivo and obtaining the monoclonal antibody from the culture medium. In the case of in vivo production, the culture medium is ascitic fluid.

Methods for raising and for screening hybridomas and monoclonal antibodies are well known to those skilled in the art. The general methodology is set out by Kohler & Milstein (1975) and there have been numerous publications on the subject since then. Any such method may be used to raise and to screen hybridomas and monoclonal antibodies according to a method of the present invention. The antigen used to raise the antibodies may be wild type HBsAg or a mutant form of HBsAg, for example, as described above, for example, one or more of the mutant forms I to IV described above. The screening of the resulting hybridomas and monoclonal antibodies for their ability to bind specifically to different forms of HBsAg may be carried out by any conventional method using wild type HBsAg and the chosen mutant forms. As described above, screening may carried out using, as reference antigens, wild type HBsAg and two or more mutant forms of HBsAg, for example, as described above, for example, two or more of the mutant forms I to IV.

For screening, it is particularly convenient to use an IgG reverse capture radioimmunoassay, which is capable of a very low background and a large dynamic range, and has the further advantage of being simple to set up.

In an IgG reverse capture assay for an antibody of interest, an appropriate anti-species IgG is immobilised on a solid phase, for example, microwells. If, for example, the antibodies under investigation have been raised in mice, then the solid phase is coated with anti-mouse IgG. The sample under investigation is then incubated with the immobilised anti-species IgG, whereupon a representative proportion the total IgGs present in the sample are captured. The solid phase is then incubated with an appropriate labelled antigen, which forms a complex only with the captured antibody of interest. Any complexes formed may then be detected.

In the present case, a sample under investigation, for example, a tissue culture supernatant fluid from a hybridoma culture or ascitic fluid, is incubated with immobilised anti-IgG. The captured antibodies are incubated separately with labelled wild type HBsAg and with two or more labelled mutant HBsAgs, for example, as described above, for example, selected from mutant forms I to IV. Any sample that is capable of binding specifically wild type HBsAg and two or more mutant surface antigens contains a monoclonal antibody that falls within the present invention.

A reverse phase IgM or IgA assay may be used analogously to obtain an IgM or IgA monoclonal antibody.

Commercially available immunoassays for HBsAg are generally heterogeneous phase or "capture" assays, in which anti-HBs is immobilised on a solid phase, usually microwells, small particles or beads. When a sample under investigation, generally serum, is contacted with the immobilised anti-HBs, HBsAg present in the sample should bind to the immobilised antibody. The captured antigen is then detected, generally using a labelled anti-HBs. In conventional assays, the antibody used for capture or for detection may be monoclonal or polyclonal.

Polyclonal antibodies, because of their nature, have a range of specificity and selectivity. In the case of HBV, this may result in the presence in the antiserum of an antibody that can bind to an escape mutant. However, that cannot be guaranteed, and there is an inherent problem in obtaining uniformity of product from batch to batch. Monoclonal antibodies have defined specificity and selectivity and may therefore fail to detect escape mutants.

The use of a monoclonal antibody of the present invention, which is capable of binding specifically to both wild type HBsAg and to mutant HBsAg, or a combination of two or more such antibodies, including fragments and derivatives thereof, in an immunoassay for HBsAg improves the performance of the assay and reduces the possibility that mutant HBsAg will not be detected. A monoclonal antibody of the present invention or a combination of two or more such antibodies may be used either as the only anti-HBs antibody reagent or, preferably, may be used in addition to polyclonal anti-HBs or other monoclonal anti-HBs, for antigen capture and/or for detection of any resulting antibody-antigen complex. A monoclonal antibody of the present invention, or a combination of two or more thereof, may be used analogously to conventional anti-HBs in a homogeneous phase assay for HBsAg. The present invention accordingly provides an immunoassay for the detection of HBsAg, which comprises contacting a sample suspected of containing HBsAg with a monoclonal antibody of the present invention, a fragment or derivative thereof, or a combination of two or more thereof, and detecting any resulting antigen-antibody complex. The monoclonal antibody, fragment, derivative or combination thereof may be used as the only anti-Hbs reagent or may be used with one or more other anti-HBs antibodies selected from polyclonal anti-HBs and other anti-HBs monoclonal antibodies.

Immunoassays of various different formats, methods for carrying them out and suitable reagents are a well known and are described in various textbooks and review articles, for example, Kemeny & Challacome 1988 and Tsu & Herzenberg 1980. Any method for the detection of an antigen may be used in the present invention.

An assay according to the present invention may be a so-called "sandwich" assay, a competition assay or a direct reaction. The monoclonal antibody, fragment, derivative or combination thereof may be immobilised on a solid surface alone or in admixture with a polyclonal anti-HBs antiserum and/or with one or more other anti-HBs monoclonal antibodies. Alternatively the monoclonal antibody of the invention or the combination thereof and any further antibodies may be in a homogeneous phase. Any resulting antibody-antigen complex may be detected using labelled anti-HBs. In the case of a heterogeneous phase assay, the anti-HBs used for detection may be the same as or different from that used for coating the solid surface.

Suitable solid surfaces on which anti-HBs may be immobilized are well known and include the inner walls of wells of microtitre plates, beads, particles and so-called "latex". Membranes and strips, for example, of nitrocelluose or paper may be used. A membranes or strip may be incorporated in an assay device. Such devices are also well known. The invention includes such solid phases on which a monoclonal antibody of the present invention, or a fragment or derivative thereof, or a combination of two or more thereof is immobilised.

The anti-HBs used for detection of any antigen-antibody complex may be labelled with any agent capable of generating a signal directly or indirectly. Such agents are well known. Agents capable of generating a direct signal include radiolabels, chromogenic and fluorescent labels. Agents capable of generating a signal indirectly include enzymes capable of catalysing a reaction that gives rise to a colour change.

The present invention also provides a kit which comprises the components requires to carry out an immunoassay of the present invention. Such a kit comprises, for example, a monoclonal antibody of the present invention or a combination of two or more thereof immobilised on a solid surface, together with container(s) comprising other reagent(s) required, for example, selected from washing solutions and diluents, standard solutions and control reagents, labelled anti-HBs antibodies and, in the case of enzyme-labelled anti-HBs, colour reagents.

Often an immunoassay for antibodies to hepatitis B core protein (HBc) is carried out simultaneously with the assay for HBs, for example, in the same microwell. The present invention includes the use of a monoclonal antibody of the present invention in such assays, and kits and coated solid phases for use with such assays.

As indicated above, a monoclonal antibody of the present invention may be used for passive immunisation, for example, during liver transplantation of an HBV infected patient. For passive immunisation, the antibody is brought into a suitable form for use as an antiserum for parenteral administration, for example, in a form allowing derivatisation including humanization. The dose of antibody to be used will depend on the particular circumstances of each patient and will be determined on a case-by-case basis.

A monoclonal antibody of the present invention, including combinations of two more such antibodies, fragments and derivatives thereof, may be used alone or in addition to other anti-HBs antibodies, either polyclonal or monoclonal. Other anti-HBV antibodies may also be included.

A mutant form of HBsAg to which a monoclonal antibody of the present invention binds may itself be used as an antigen, for example, as a vaccine; in the production of monoclonal antibodies; and for screening for putative antibodies according to the present invention. Such a mutant HBsAg may be obtained from a subject believed to be harbouring an HBV escape mutant. Such a subject will generally be both anti-HBs positive and HBsAg positive. Suitable subjects may be found among patients who have received monoclonal antibody therapy for HBV infection, in vaccinated subjects, especially where breakthrough infection is found, and in cases of HBV infection that are difficult to diagnose in clinical laboratories using current standard tests.

A mutant form of HBsAg, for example, one of the mutant forms described above, for example, mutant forms I to IV, may be produced by recombinant DNA technology. Naturally occurring DNA encoding the mutant form may be inserted into an appropriate host for expression of the mutant HBsAg. Alternatively, wild type DNA may be modified, for example, by site-directed mutagenesis, and then used to obtain expression of a mutant form.

HBsAg obtained from natural sources, generally from the blood of a selected subject, will have natural glycosylation, and it is generally preferable to use such HBsAg as an antigen. Methods of purifying HBsAg from blood are well known, see for example, Cameron et al. 1980. It may be preferable to produce a recombinant mutant HBsAg that is partially or fully glycosylated.

The HBsAg may be full-length or an appropriate antigenic fragment may be used. Such a fragment may be obtained by recombinant technology. Alternatively, a fragment that is an antigenic peptide, for example, produced by chemical synthesis may be used. For use as a vaccine, an antigen should be immunogenic ie capable of producing a protective response.

For use in a vaccine, the desired antigen (whether full length, fragment or peptide), and whether obtained recombinantly, synthetically or from natural sources) must be purified and brought into a suitable form, for example, using conventional carriers and, where appropriate, adjuvants.

As an alternative to using an antigen for vaccination, a nucleic acid encoding the antigen may be used. Methods for presenting a nucleic acid in a form from which it can be expressed in vivo are known. The present invention includes a nucleic acid vaccine.

Methods for producing anti-idiotype antibodies are well known. In the present case a monoclonal antibody of the present invention is used as the antigen in the production of an anti-idiotype antibody, and the resulting antibodies may be screened against a monoclonal antibody of the present invention. An anti-idiotype antibody of the present invention may itself be used as a vaccine, in known manner.

The following non-limiting Example illustrates the present invention.

Hybridoma P2D3 was deposited with the Centre for Applied Microbiology and Research, Salisbury, Wiltshire SP4, OJG, United Kingdom on Apr. 23, 1997 under the terms of the Budapest Treaty and received accession no. ECACC 97042331. Further, hybridoma M3A10 was deposited with the Centre for Applied Microbiology and Research, Salisbury, Wiltshire SP4, OJG, United Kingdom on Apr. 23, 1997 under the terms of the Budapest Treaty and received accession no, ECACC 97042330, and hybridoma M4F5 was deposited with the Centre for Applied Microbiology and Research, Salisbury, Wiltshire SP4, OJG, United Kingdom on Apr. 25, 2007 under the terms of the Budapest Treaty and received accession no. 97042519.

EXAMPLE

I. Materials and Methods

1: Patients

The monoclonal antibodies described below were raised against the mutant HBsAg of two patients. Those patients were identified as a result of inconsistent serological markers.

Patient MAM was an HBV carrier. The serum was initially, in 1986, HBsAg positive by the polyclonal based reverse passive haemagglutination assay (RPH) but negative by a monoclonal enzyme immunoassay (EIA). In 1988 the patient underwent renal transplantation. When tested again, HBsAg became detectable by both polyclonal and monoclonal antibody based assays but reverted to being detectable by polyclonal antibody assay only. The patient's serum was anti-HBc and HBsAg positive throughout the period of follow-up.

Patient NP underwent renal transplantation in 1985. In 1990 the patient was anti-HBc sero-positive but HBsAg and anti-HBs were not detected. Haemodialysis was started in 1993 and later that year HBsAg was detected by polyclonal based assays only.

Neither of the patients had been previously vaccinated.

The sequences of the HBsAg genes around the "a" determinant were determined by single stranded sequencing carried out directly on PCR products as is described in Hawkins et al., 1994.

2: Production of Monoclonal Antibodies 2.1: Animals

Female Balb/c mice used.

2.2: Purification of HBsAg

Purification of HBsAg required for immunisation of mice was based on the method described by Cameron et al., 1980.

High titre HBsAg positive serum was fractionated by passing 20 ml volumes through a 100×5 cm diameter column of Sepharose 6B (Pharmacia Ltd) equilibrated with 0.9% NaCl pH 7.6 buffered with Tris and containing 0.1% sodium azide (Tris/Sal/Az). The HBsAg rich fractions, now free of albumin and IgG, were concentrated to a volume of 9 ml by ultrafiltration in a stirred 200 ml ultrafiltration cell fitted with an XM 100 A membrane (Amicon Ltd.). To this 2.69 g of solid CsCl were added and the volume adjusted to 10 ml to give a density of 1.2 g/cm$^3$. The material was then ultra-centrifuged for three days at 124000 g in two 5 ml tubes in a SW50-L swinging bucket rotor (Beckman RIIC Ltd) at 20° C. to give isopyknic banding in the self forming density gradient.

The main HBsAg band containing the 22 nm small particles was removed from both tubes, pooled and made up to 5 ml with a solution of CsCl in Tris/Sal/Az (2.885 g plus 10 ml) which gave a final density of 1.2 g/cm$^3$. The material was ultra-centrifuged under the same conditions as before in one 5 ml tube to give the second isopyknic banding. The final HBsAg band was removed and dialysed in PBS to remove CsCl.

3: Immunisation of Animals

Fifty microlitres of purified NP HBsAg mixed in an equal volume of Titermax adjuvant (Vaxcel, Inc.) were injected subcutaneously into a female Balb/c mouse. Approximately two months later a dose of 30 µl was given intraperitoneally (i.p) followed three months later by a 75 µl dose also given i.p. The final 25 µl of HBsAg in saline were given intravenously three days before the fusion.

The same protocol was used when immunizing the mouse with the MAM HBsAg.

4: Culture of Myeloma Cells

JK cells derived from P3-X63-Ag8653 (Kearney et al., 1979) were cultured in complete medium (see reagents) at 37° C. in a 5% $CO_2$ in air atmosphere at 100% humidity.

The cells were split 1:2 approximately three times weekly and maintained at a concentration of between $2 \times 10^5$ and $2 \times 10^6$ cells per ml. Only cells in the log phase of growth were used for fusion to splenocytes.

For the fusion, the myeloma cells were spun at 1,500 g for 10 minutes and washed three times in the same volume of incomplete medium (see Reagents). The resuspended JK cells were diluted 1:10 in incomplete medium and the viability and concentration of the cells determined by counting the cells using a Neubauer chamber. The concentration of JK cells was found to be approximately $5.87 \times 10^7$ cells/ml.

4.1: Preparation of Feeder Cells

Mouse peritoneal exudate cells were used as a feeder cell layer for hybrid cells. These were prepared the day before the fusion was undertaken. Cold complete medium containing hypoxanthine, aminopterin and thymidine (HAT medium-see reagents) was used for preparation of the feeder cells. Five milliliters of the medium was injected into the peritoneal cavity of a freshly killed Balb/c mouse and after gentle agitation was removed aseptically now containing exudate cells. One hundred microliters of the cells were added to each well of a sterile 96 well plate (4-5 plates were needed per spleen to be fused). All plates were examined on the day of the fusion to ensure that they free from any visible bacterial or fungal contamination.

4.2: Preparation of Spleen Cells

Preparation of Spleen Cells from Both MAM HbsAg immunised and the NP HBsAg immunised mice were carried out in a similar method.

The spleen was carefully removed from the freshly killed mouse and placed in a petri dish containing 5 mls of cold complete medium. The spleen was disrupted carefully with the blunt side of a scalpel blade thus teasing away the cells from the spleen connective tissue. The cell suspension was then transferred to a sterile universal container and the debris allowed to settle to the bottom. The supernatant was carefully removed and the cells pelleted at 150 g for 10 minutes. The cells were washed three times in 10 ml of incomplete medium and the final cell pellet was resuspended in 10 ml of incomplete medium. The yield and viability of the spleen cells was determined using a Neubauer chamber. Approximately $7 \times 10^7$ cells were harvested from the NP spleen whilst $10 \times 10^7$ cells were obtained from the first MAM spleen and $2.5 \times 10^7$ cells from the second MAM spleen.

4.3: Cell Fusion

The splenocytes were mixed with the myeloma cells at a 4:1 ratio and the mixture centrifuged at 1500 g for 10 minutes. The supernatant was removed leaving a dry pellet of cells at the bottom the container. This was placed in a water bath at 37° C. Polyethylene glycol 1540 (PEG) which had been previously sterilised by autoclaving was also warmed in the 37° C. waterbath. The cell pellet was loosened in the bottom of the container and 1 ml of the PEG solution added dropwise whilst the container was gently agitated. The cell/PEG mix was left at 37° C. for one minute and then an additional 2 ml of the warm incomplete medium added. Further incomplete medium was added slowly so that the volume doubled every minute until 25 ml of incomplete medium had been added. The fused cells were then centrifuged at 1500 g for 10 minutes and the pellet resuspended in 10 ml of HAT medium. The cell suspension was distributed evenly over five plates of feeder cells and then placed in a $CO_2$ incubator.

4.4: Culture of Hybrid Cells

Clusters of growing fused cells appeared after about a week. At this stage the cells were re-fed by replacing 100 μl of old medium with fresh HAT medium. Approximately 14 days after the fusion, 100 μl of the supernatant fluid from each well where successfully fused clusters of cells were found, was removed and assayed for the presence of anti-HBs. The supernatant was replaced with complete medium containing hypoxanthine and thymidine (HT medium-see Reagents).

4.5: Reverse Capture RIA for the Detection of Anti-HBs Secreting Hybridomas

Supernatant from viable hybridoma cultures were tested for anti-HBs on the basis of a reverse capture assay.

Round bottom Nunc microwells were coated with 100 μl of a 1:1000 dilution in Tris buffer of the IgG fraction of rabbit anti-mouse IgG. After two days at room temperature the wells were washed with Tween Saline and quenched for one hour with 0.5% bovine serum albumin in Tris buffer (Tris BSA buffer-see reagents). The wells were then sealed and stored moist at 4° C. All washings were done with Tween Saline.

Before the assay was carried out, the Tris BSA buffer was removed. One hundred microliters of a 1:10 dilution in phosphate buffered saline of the supernatant from each well where successfully fused clusters of cells were found was added to the assay wells and incubated at 37° C. for one hour. After washing, 100 μl of purified $^{125}$I-wild type HBsAg were added and left in a moist box at room temperature overnight. The assay wells were then washed and bound reactivity measured in a sixteen channel gammacounter. Supernatant containing anti-HBs gave an increased binding of the label. The hybridomas were subsequently retested by the same assay using $^{125}$I-MAM and $^{125}$I-NP labels instead of $^{125}$I-wild type HBsAg. Each assay carried out included positive and negative controls. Positive controls used were monoclonals D2H5 and H3F5 raised against wild type HBsAg. An anti-HIV gag monoclonal 3D3F2 and phosphate buffered saline were used as negative controls.

From the results of the assay, parent wells containing colonies secreting anti-HBs were chosen for further screening and cloning.

When the cells were growing well, they were aspirated using a glass pasteur pipette and transferred aseptically to 24 well sterile plates which contained a layer of mouse peritoneal exudate cells (PEC) in HT medium.

4.6: Cloning by Limiting Dilution

Hybridomas identified as anti-HBs positive were cloned by limiting dilution. This is done to ensure that the antibody secreted is homogenous and monospecific. For each hybrid culture the volume of cell suspension containing 100 cells was calculated and this volume added to 10 ml of complete medium. One hundred microliters of this cell suspension was added to each of 48 wells of a 96 well plate containing feeder cells in complete medium. One hundred more cells were added to the remaining 5 ml of complete medium and 100 μl of this more concentrated cell suspension were added to 24 wells of the plate. Finally, a further 100 cells were added to the remaining cell suspension and this was distributed over the last 24 wells. Variation in the concentration of cells on each plate made allowance for inaccurate cell counts and low viability of some cultures. This procedure was repeated for each selected parent hybridoma.

Approximately five days after cloning the plates were examined for wells where only a single colony was visible. One hundred microliters of supernatant was removed from these wells and retested for anti-HBs using the reverse capture assay described previously.

Clones secreting anti-HBs were then expanded as before and re-fed as necessary by removal of 100 μl of tissue culture supernatant and replaced with fresh complete medium.

4.7: Culture of Hybrid Clones

Once the colonies were large enough to cover the well they were expanded into 12 $cm^2$ tissue culture flasks containing feeder cells and then further into 25 $cm^2$ and 75 $cm^2$ flasks. The cells were split 1:2 approximately every 2-3 days with fresh complete medium.

Once good growth had been established, some of the cells were frozen and stored under liquid nitrogen in incomplete medium supplemented with 10% dimethyl sulphoxide and 50% foetal calf serum.

4.8: Production of Ascitic Fluid

Female Balb/c mice, aged 12-20 weeks were primed with 0.5 ml pristane. One to four weeks after priming, 1 ml of cloned hybridoma cells, resuspended in incomplete medium, were injected intraperitoneally. The ascitic fluid was aspirated 1-3 weeks later and separated from cells by centrifugation at 3000 g for 10 minutes. The ascitic fluid was then stored at −20° C.

II. Characterisation of the Monoclonal Antibodies Raised Against Wild Type and Mutant HbsAg

1: Isotyping of Monoclonal Antibodies

Isotyping of the monoclonal antibodies was carried out using a kit from Serotec (Serotech Limited, 22 Bankside Station Approach, Kidlington, Oxfords OX5 1BR) specifically designed to identify the class and subclass of monoclonal antibodies in tissue culture supernatants. Used in accordance with the manufacturer's recommendations, it readily characterised the mouse monoclonal antibody.

2: Serum Protein Electrophoresis

Ascitic fluid from each clone was tested for the presence of a monoclonal protein band by serum protein electrophoresis (SPE, Paragon Electrophoresis System, Beckman Ltd). Following the protocol provided, the kit conveniently identified those ascitic fluids containing high levels of monoclonal immunoglobulin.

The Paragon Serum Protein Electrophoresis kit is intended for the electrophoretic separation of proteins in a buffered agarose gel. After electrophoresis, the proteins in the gel were immobilised in a fixative solution and the gel dried to a film. The protein pattern is visualised by staining the film with a protein-specific stain and the pattern visually interpreted.

3: Immunoglobulin G Preparation

Immunoglobulin G was prepared by ion exchange chromatography from the various ascitic fluids.

DE52 gel (Whatman Ltd), supplied pre-swollen was resuspended in a 0.2M phosphate buffer pH 8.0. The gel was then dispersed in distilled water to give a 10 mM buffer strength.

A K9 column (Pharmacia) was packed with the DE52 gel to give a gel to sample volume ratio of 5:1. All columns were equilibrated with an equal volume of 10 mM phosphate buffer (PB-see reagents). After overnight dialysis at 4° C. in 10 mM PB, the sample was layered on top of the columns and allowed to absorb over 30 minutes.

Immunoglobulin G from the ascitic fluid was recovered by stepwise elution with 10 mM, 30 mM and 60 mM PB. Each buffer was allowed to run through the column and the optical density of the eluent was monitored and recorded at 280 nm (Ultra Violet Spectrophotometre, LKB Ltd.). The three different eluents were collected separately and assayed for anti-HBs activity in the reverse capture RIA. The eluent containing the majority of anti-HBs reactivity could be identified.

The protein concentrations of the ascitic fluid IgG were calculated by determining their absorbance at 280 nm using an El % 1 cm value of 1.4 in a spectrophotometer.

4: Immunoglobulin A Preparation

As with IgG, IgA was prepared using ion exchange chromatography. Separation was, however, carried out on a Sephacryl gel. As with DE52, the gel was equilibrated with 10 mM phosphate buffer. The sample was layered on top of the column and allowed to absorb over 30 minutes. As before, the ascitic fluid was separated by stepwise elution. The eluent was monitored and then tested for anti-HBs reactivity.

5: Radiolabelling Procedure

Labelling of the immunoglobulin fractions was carried out by the iodogen method (Salacinski et al., 1979).

Clean 7.5×10 cm glass tubes were initially coated with 5 μg of chloroform. To the iodogen tubes 15 μg of protein in PBS was added. Finally Na$^{125}$I (0.5 mici, Amersham International Plc) was added and the reaction in the tube allowed to proceed for 10 minutes on ice. The iodogen acts as a mild oxidising agent for the Na$^{125}$I to bind onto a tyrosine residue on the protein.

A K9 column was then packed with Sephadex G-25 and equilibrated in Tris BSA buffer. Non-radioactive iodide (KI/NaI) in PBS was added to the G25 column as this reduced the tendency for free $^{125}$I to stick to the column. The reaction mixture was then removed from the iodogen tube and transferred to the column. Tris BSA buffer was then used for eluting and the eluent monitored. The $^{125}$I-labelled protein fraction was collected from the first peak and stopped as the peak began to tail off. The labelled protein was then stored at 4° C. in Tris saline buffer containing 5% BSA.

Elution was continued until free $^{125}$I had come through (i.e. the second peak). The height of this peak compared to the height of the first peak gave an estimate of the percentage of $^{125}$I bound.

III. Results

1: Patients

The sera from both patients MAM and NP were tested in a series of assays for HBsAg. Results of the comparison of monoclonal and polyclonal antibody based methods is shown in Table 1 below.

TABLE 1

HBsAg assay detection: a comparison

| Patient | Assay 1 | Assay 2 | Assay 3 | Assay 4 | Assay 5 |
|---------|---------|---------|---------|---------|---------|
| NP      | +       | −       | +       | +       | +       |
| MAM     | +       | −       | +       | nt      | nt      |

Key to Table 1:
Assay I    Reverse passive haemagglution assay.
Assay II   Monoclonal based antibody assay.
Assay III  Mixed monoclonal/polyclonal based assays.
Assay IV   Mixed monoclonal/polyclonal based assays.
Assay V    Monoclonal based antibody assay.

Results from the sequencing revealed several point mutations in the "a" determinant of both patients. Mutations were found in HBV DNA amplified from patient NP (subtype ayw) at surface antigen codons encoding amino acids 133, 134 and 144. Mutations were found at codons encoding amino acids 133, 134, 142, 144 and 145 in HBV DNA amplified from patient MAM (subtype adr). Those mutations were detected both before and after transplantation. The sequences did not differ between the period when HBsAg was detectable by either polyclonal antibody based assays alone as compared with the time when HBsAg was detectable by both monoclonal and polyclonal based assays. The mutations are shown in Table 2.

MAM HBsAg is Mutant HBsAg I and NPHBsAg is Mutant HBsAg II. The complete amino acid sequence of, and nucleotide sequence encoding, HBsAg is given in Valenzuela et al. (1979).

TABLE 2

Mutations detected in the HBsAg "a" determinant of patients MAM and NP

| Patient | Codon | Wild Type Codon | Wild Type Amino Acid | Mutant Codon | Mutant Amino Acid |
|---------|-------|-----------------|----------------------|--------------|-------------------|
| NP      | 133   | ATG             | Methionine           | ATT          | Isoleucine        |
|         | 134   | TAT             | Phenylalanine        | CAT          | Histidine         |
|         | 144   | GAT             | Aspartic Acid        | GTC          | Valine            |
| MAM     | 133   | ATG             | Methionine           | ATC          | Isoleucine        |
|         | 134   | TAT             | Phenylalanine        | AAT          | Asparagine        |
|         | 142   | CCT             | Proline              | AGT          | Serine            |
|         | 143   | TCG             | Serine               | TTG          | Leucine           |
|         | 145   | GGA             | Glycine              | AAA          | Lysine            |

2: Identification and Distribution of Anti-Hbs Secreting Monoclonal Antibodies

Hybridomas secreting anti-HBs were initially identified by using the reverse capture assay (see section II, 4.5). Approximately a week after the fusion all wells containing clusters of growing cells were tested for anti-HBs activity. Every assay performed included both negative and positive controls.

Cells arising from the HAM fusion were tested in the RIA in the first instance with the $^{125}$I MAM HBsAg whilst those from the NP fusion were tested with the $^{125}$I NP HBsAg. Results of the assay would give an indication of those clones which were producing antibodies against their respective surface antigens. Hybridomas which gave counts above 750 cpm were considered to be positive. It was shown that of the 320 MAM clones tested, 10% were positive whilst 8% of the 200 NP clones were found to be positive.

To check for any reactivity against the wild type (WT) HBsAg, clones from both the NP and MAM fusions, regardless of whether they were positive in the previous assay were tested in the reverse capture RIA using $^{125}$I WT HBsAg label. As before, a positive result was indicated by an increased binding of the label. Hybridomas which gave counts over 650 cpm were considered as positive. Of the 320 MAM clones tested, 6% gave positive results whilst 4% of the NP clones were found to bind to the $^{125}$I WT HBsAg.

With the results obtained thus far it was possible to identify those clones secreting anti-HBs which was specifically recognising and therefore binding either MAM, NP or WT hepatitis B surface antigen.

To determine if there was any cross reactivity within these hybridomas the NP clones were tested with $^{125}$I MAM HBsAg and the MAM clones with the $^{125}$I NP HBsAg. It was found that 4 of the MAM clones recognised NP label whilst 5 of the NP clones were recognised by the MAM label.

The clones had now been tested with all label combinations. It was therefore possible to identify those hybridomas which had consistently given strong positive results be it with the $^{125}$I MAM, $^{125}$I NP or $^{125}$I WT HBsAg. The monoclonal antibodies could now be divided into the following categories: 1) MAM specific; 2) NP specific; 3) MAM/NP specific; 4) MAM/WT specific; 5) NP/WT specific; 6) NP/WT/MAM specific.

Eight NP and ten MAM parent hybridomas each of which fell under one of the categories listed above were chosen. These hybridomas were chosen as they displayed good cell growth as well as being repeatedly positive when tested for anti-HBs activity.

The eighteen chosen hybridomas were then cloned by limiting dilution. Approximately fourteen days after cloning, wells containing single colonies were tested in the reverse capture assay with all three of the labels. Six of the eight NP hybridomas cloned successfully and were found to be still positive for anti-HBs activity.

However, with the MAM clones, it was found that only six of the ten chosen hybridomas cloned. Attempts at recloning the hybridomas from their respective parent colonies proved unsuccessful despite increasing the concentration of the cells added to each plate. The six successfully cloned hybridomas containing single colonies were tested for anti-HBs activity. From the six, two hybridomas, M3C9 and M3A10, both three way crosses were found to be still positive for anti-HBs. Hybridomas derived from the MAM fusion were proving to be extremely unstable as they were passaged.

At least three positive clones were chosen from each hybridoma for expansion. The clones were propagated in culture and retested two weeks later. All the NP clones were still positive for anti-HBs secretion. However of the MAM clones, M3C9 had also proved to be extremely unstable giving negative results in the RIA.

The final positive secreting hybridomas from each fusion are shown in Table 3 below. The table also gives the monoclonal antibody specificity and their RIA values rounded up to the nearest 500 cpm.

TABLE 3

Clones derived from NP and MAM fusions with their respective specificity and RIA values

| Clone | Binding of $^{125}$I HBsAg (cpm) WT | MAM | NP | Clone specificity |
|---|---|---|---|---|
| *P2D3 | 4000 | 6000 | 3500 | WT/NP/MAM cross |
| P2C6 | neg | 5000 | 3000 | NP/MAM cross |
| P2H6 | 2000 | neg | 11000 | NP/WT cross |
| P2H9 | neg | neg | 1000 | NP only |
| P4C11 | neg | neg | 10000 | NP only |
| P3E4 | 1000 | neg | 10000 | NP/WT cross |
| *M3A10 | 3000 | 5000 | 2500 | WT/NP/MAM cross |
| Control D2H5 | 7000 | neg | 2000 | WT/NP cross |
| Control H3F5 | 6000 | 1000 | neg | WT/MAM cross |

Where P represents the hybridomas derived from the NP fusion and M represents the hybridomas derived from the MAM fusion.
*Denotes three-way cross.

A second MAM fusion was undertaken. The fusion was carried out as described before. However, the yield of spleen cells was only 25% of that recorded in the original MAM fusion. Approximately a week later, all wells containing clusters of growing cells were tested for anti-HBs activity using the reverse capture RIA. As before, each assay performed included negative and positive controls. All cells arising from the fusion were tested with each of the labels, $^{125}$I MAM HBsAg, $^{125}$I NP HBsAg and $^{125}$I WT HBsAg.

Of the 68 cloned tested, only three produced positive results. One clone was found to be MAM specific whilst the other two, M4H2 and M4F5, were found to be WT/NP/MAM crosses (Table 4). However, as described in more detail below, M4H2 proved to be unstable, like some of the hybridomas from the first MAM fusion. It eventually stabilised as a MAM-specific clone.

TABLE 4

Clones derived from second MAM fusion with their respective specificities and RIA values

| Clone | Binding of $^{125}$I HBsAg (cpm) WT | MAM | NP | Clone specificity |
|---|---|---|---|---|
| M4B12 | neg | 7000 | neg | MAM only |
| **M4H2 | 9000 | 8000 | 1500 | WT/NP/MAM cross |
| *M4F5 | 10000 | 9000 | 10000 | WT/NP/MAM cross |
| Control D2H5 | 10000 | neg | 2000 | WT/NP cross |
| Control H3F5 | 10000 | 7000 | neg | WT/MAM cross |

*Denotes three-way cross
**Initially found to be a three-way cross but was later found to be unstable and changed to a MAM-specific clone, see below.

All three of the hybridomas displayed good cell growth and were cloned by limiting dilution. Cloning on this occasion proved successful and all wells containing single colonies were tested in the reverse capture RIA with all three of the labels. The clones were still found to be positive for anti-HBs activity.

Five positive clones were chosen for expansion. After further growth in culture, the clones were screened and found to be still positive for anti-HBs production.

The final number of positive parent hybridomas and their antibody specificity and cross-reactivity obtained from the NP and the two MAM fusions are shown in Table 5.

TABLE 5

Final number of clones with their respective specificities and RIA values.

Binding of $^{125}$I HBsAg (cpm)

| Clone | WT | MAM | NP | Clone specificity |
|---|---|---|---|---|
| *P2D3 | 4000 | 6000 | 3500 | WT/NP/MAM cross |
| P2C6 | neg | 5000 | 3000 | NP/MAM cross |
| P2H6 | 2000 | neg | 11000 | NP/WT cross |
| P2H9 | neg | neg | 1000 | NP only |
| P4C11 | neg | neg | 10000 | NP only |
| P3E4 | 1000 | neg | 10000 | NP/WT cross |
| *M3A10 | 3000 | 5000 | 2500 | WT/NP/MAM cross |
| M4B12 | neg | 7000 | neg | MAM only |
| **M4H2 | 9000 | 8000 | 1500 | WT/NP/MAM cross |
| *M4F5 | 10000 | 9000 | 10000 | WT/NP/MAM cross |
| Control D2H5 | 10000 | neg | 2000 | WT/NP cross |
| Control H3F5 | 10000 | 7000 | neg | WT/MAM cross |

Key to table 5:
*Denotes three-way cross
**Initially found to be a three-way cross but was later found to be unstable and changed to a MAM-specific clone, see below.

Further cross-competition studies were carried out using antibodies P2D3, M4F5 and M3A10 with WT, NP and MAM HBsAg. Each of those antibodies cross-competed with each other, but did not cross-compete with any of the other monoclonal antibodies raised. At this stage M4H2 still appeared to be a three-way cross.

These results further indicate that the monoclonal antibodies of the invention bind to a distinct epitope.

One positive clone from each hybridoma parent was chosen and injected into a previously pristane primed Balb/c mouse. One to three weeks after the intraperitoneal inoculation, the ascitic fluid was harvested from the mice. All clones successfully produced ascitic tumours in the mice. The quantity of ascitic fluid obtained from each mouse varied from 1 ml to 5 ml.

More extensive cross-competition studies were carried out using various different antibodies, each with WT, MAM and NP HBsAg. Those tests were carried out according to the reverse capture RIA protocol given above with the following modifications: the microwells were coated with a goat polyclonal anti-HBs antibody. In each case 100 μl of the antigen were added and incubated overnight, then 50 μl each of $^{125}$I labelled and unlabelled monoclonal antibody were added and binding was determined. The results are presented in Tables 6a, 6b and 6c. In those Tables, the labelled antibodies are listed horizontally and the unlabelled antibodies are listed vertically.

TABLE 6a

WT HBsAg (1:3 K)

|  | P4C11 | P3E4 | P2D3 | P2H6 | P2H9 | P2C6 | M4F5 | M4H2 | M3A10 | D2H5 | H3F5 |
|---|---|---|---|---|---|---|---|---|---|---|---|
| P4C11 | − | − | − | +++ | − | − | − | − | − | − | − |
| P3E4 | − | +++ | − | +++ | − | − | − | − | − | − | − |
| P2D3 | − | − | +++ | +++ | − | − | +++ | − | +++ | − | − |
| P2H6 | − | − | − | +++ | − | − | − | − | − | − | − |
| P2H9 | − | − | − | +++ | − | − | − | − | − | − | − |
| P2C6 | − | − | − | +++ | − | − | − | − | − | − | − |
| M4F5 | − | − | +++ | + | − | − | +++ | − | +++ | − | − |
| M4H2 | − | − | − | +++ | − | − | − | − | − | − | − |
| M3A10 | − | − | +++ | +++ | − | − | +++ | − | +++ | − | − |
| D2H5 | − | − | − | − | − | − | − | − | − | +++ | − |
| H3F5 | − | − | − | − | − | − | − | − | − | − | +++ |
| percentage binding | 0.4 | 1.0 | 4.8 | 0.4 | 0.1 | 0.1 | 14 | 0.1 | 0.3 | 37 | 23 |

+++ >75% inhibition
++ 50-75% inhibition
− <50% inhibition

TABLE 6b

MAM HBsAg (1.3k)

|  | P4C11 | P3E4 | P2D3 | P2H6 | P2H9 | P2C6 | M4F5 | M4H2 | M3A10 | D2H5 | H3F5 |
|---|---|---|---|---|---|---|---|---|---|---|---|
| P4C11 | − | − | − | − | − | − | − | − | − | − | − |
| P3E4 | − | − | − | − | − | − | − | − | − | − | − |
| P2D3 | − | − | +++ | − | − | − | +++ | − | ++ | − | ++ |
| P2H6 | − | − | − | − | − | − | − | − | − | − | − |
| P2H9 | − | − | − | − | − | − | − | − | − | − | − |
| P2C6 | − | − | − | − | − | − | − | − | − | − | − |
| M4F5 | − | − | +++ | − | − | − | +++ | − | ++ | − | − |
| M4H2 | − | − | − | − | − | − | − | +++ | − | − | ++ |
| M3A10 | − | − | ++ | − | − | − | +++ | − | ++ | − | − |
| D2H5 | − | − | − | − | − | − | − | − | − | − | − |
| H3F5 | − | − | − | − | − | − | − | +++ | − | − | +++ |
| Percentage binding | 0.1 | 0.3 | 6.7 | 0.4 | 0.3 | 2.2 | 21 | 14 | 0.8 | 0.2 | 23 |

+++ >75% inhibition
++ 50-75% inhibition
− <50% inhibition

TABLE 6c

NP HBsAg (1:150)

|  | P4C11 | P3E4 | P2D3 | P2H6 | P2H9 | P2C6 | M4F5 | M4H2 | M3A10 | D2H5 | H3F5 |
|---|---|---|---|---|---|---|---|---|---|---|---|
| P4C11 | +++ | − | − | +++ | − | − | − | ++ | − | − | − |
| P3E4 | − | +++ | − | − | +++ | − | − | − | − | − | − |
| P2D3 | − | − | +++ | ++ | ++ | − | +++ | − | − | − | − |
| P2H6 | +++ | − | − | +++ | ++ | − | − | ++ | − | − | − |
| P2H9 | ++ | − | − | ++ | ++ | − | − | ++ | − | − | − |
| P2C6 | − | − | − | − | ++ | +++ | − | ++ | − | − | − |
| M4F5 | − | − | +++ | − | ++ | − | +++ | − | − | − | − |
| M4H2 | − | − | − | − | ++ | − | − | − | − | − | − |
| M3A10 | − | − | ++ | − | ++ | − | ++ | − | − | − | − |
| D2H5 | − | − | − | − | − | − | − | − | − | +++ | − |
| H3F5 | − | − | − | − | − | − | − | − | − | − | − |
| Percentage binding | 6 | 3 | 2 | 9 | 0.3 | 0.9 | 4 | 0.2 | 0.1 | 21 | 0.4 |

+++ >75% inhibition
++ 50-75% inhibition
− <50% inhibition

The results shown in Tables 6a, 6b and 6c confirm that the three-way cross antibodies M4F5 and P2D3 are binding to a common epitope.

M3A10 was found previously to be a three-way cross antibody (see Table 4). The fact that it is an IgA antibody (see Section III.4 below) may explain the poor binding results shown in Table 6a since this class of antibody (IgA) is difficult to purify.

As shown above, the hybridoma M4H2, which was produced in the second MAM fusion, was initially found to be a three-way cross (see Table 4). However, after further growth in culture, that hybridoma showed decreasing binding to $^{125}$I WT HBsAg and to $^{125}$I NP HBsAg. Retesting for anti-HBs activity against the WT and NP HBsAg over a period of time revealed negative results. However, M4H2 continued to recognise and bind strongly to the $^{125}$I MAM HBsAg. It appears therefore, that the clone specificity was initially unstable and with the passage of time has evolved to a MAM-specific antibody-secreting hybridoma.

Binding of $^{125}$I-labelled antibodies to various different HBsAgs was measured using a RIA in which HBsAgs was immobilised to the solid phase (microwells) via a polyclonal goat anti-HBs coated on the microwells. The HBsAgs used were WT, MAM and NP HBsAg, which have been described above, SP HBsAg and SZ HBsAg. SP HBsAg, which is serotype adw, has a mutation in the codon for amino acid 143 leading to substitution of met for ser. In SZ HBsAg, serotype adr, a mutation leads to substitution of arg for gly at position 145. (SP HBsAg is Mutant HBsAg IV and SZ HBsAg is Mutant HBsAg III.) A pool of normal human sera that has been tested and found to be hepatitis B marker free (NHS) was used as control. This is an example of an immunoassay according to the present invention. The results are presented in Table 7 below.

TABLE 7

| | % Binding of $^{125}$I- anti mutant MAb | | | |
|---|---|---|---|---|
| HBsAg | P2D3 (3 × crosses) | M4F5 (3 × crosses) | M4H2 (MAM specific) | P4C11 (NP specific) |
| WT | 12 | 15 | 0.6 | 0.1 |
| MAM | 13 | 20 | 31 | 0.2 |
| NP | 10 | 12 | 0.2 | 10 |
| SP | 23 | 26 | 0.5 | 0.4 |
| SZ | 25 | 30 | 0.4 | 0.5 |
| NHS | 0.3 | 0.2 | 0.4 | 0.3 | nt = not tested

These results show that the three-way cross antibodies detect wild type HBsAg and also HBsAg from various different mutants, including mutant HBsAg different from that used for screening the antibodies. These results further confirm that the three-way cross antibodies are binding to an epitope common to the wild type protein and to mutant forms and demonstrate the utility of the antibodies in HBsAg assays. Using such antibodies it is possible to detect the presence of escape mutants.

3: Isotyping of Monoclonal Antibodies

Isotyping of the monoclonal antibodies was carried out using a kit from Serotec. Each isotyping reagent consisted of a purified rat monoclonal antibody specific for a single class-subclass of immunoglobulin, coupled to sheep red blood cells. The coupled rat antibodies recognised the heavy chain portion of the mouse immunoglobulin. The principle of the test system was based on red cell agglutination where a positive agglutinated result was produced when highly specific antibody recognised and bound to the particular isotype to which it is directed. The binding formed a lattice on the bottom of the microtitre plate well. A negative result was produced when the reagent cells were put into a supernatant containing a class of antibody which they did not recognise. The reagent cells fell to the bottom of the well forming a small "button".

The isotype of the monoclonal antibodies are shown in Table 8.

TABLE 8

Immunoglobulin classes of monoclonal antibodies

| Monoclonal Antibody | Immunoglobulin Class |
|---|---|
| P4C11 | IgG1 |
| P3E4 | IgG1 |
| *P2D3 | IgG1 |
| P2H6 | IgG1 |
| P2H9 | IgG2 |
| P2C6 | IgG1 |
| *M3A10 | IgA |
| **M4H2 | IgG1 |
| M4B12 | IgG1 |
| *M4F5 | IgG1 |

*Denotes three-way cross
**Initially found to be a three-way cross but was later found to be unstable and changed to a MAM-specific clone, see below.

4: SPE Analysis and Purification of Anti-HBs from Ascitic Fluid

Monoclonal protein was demonstrated in the ascitic fluid of all of the clones by serum protein electrophoresis. The electrophoretic mobility of the monoclonal protein band varied slightly for each different monoclonal ascitic fluid, but was identical for different batches of ascitic fluid obtained from the same clone. The disparity in migration distance between clones was a result of the differing ionic charges on the monoclonal proteins. The intensity of staining observed in the SPE monoclonal band gave an indication of the quantity of monoclonal protein present. This varied between ascitic fluid which had been harvested from different clones. A SPE band, however, was not seen with M4B12, the MAM specific monoclonal antibody. When the recovered ascitic fluid was tested in the RIA for anti-HBs activity, a negative result was given; all the other ascitic fluids gave the expected positive results. As before the MAM specific monoclonal antibody was proving to be unstable changing from a positive secreting hybridoma to a negative. (The M4B12 parent hybridoma has since been recloned and will be retested).

Preparation of Immunoglobulin from the Ascitic Fluids was carried out as described in sections III, 3 and III, 4 above. Immunoglobulin G was prepared by ion exchange chromatography on DE52 whilst IgA was separated on a Sephacryl column. Three separate protein peaks were obtained when increasing the ionic strength from 10 mM to 30 mM and finally 60 mM PB for each monoclonal ascitic fluid. The size of the peaks varied from one monoclonal fluid to another. Eluent was collected at each peak. The anti-HBs IgG/IgA in the different buffer concentrations were then measured in the reverse capture assay with $^{125}$I MAM HBsAg, $^{125}$I NP HBsAg and $^{125}$I WT HBsAg. The assay allowed a direct comparison of results between different buffer fractions to be made. From the assay, it was possible to choose the fraction showing the highest anti-HBs activity. The protein concentrations of the chosen fractions were determined (Table 9). The quantity of IgG/IgA obtained from each monoclonal antibody varied between each batch of ascitic fluid harvested.

TABLE 9

Quantity of IgG/IgA harvested from from 1 ml of each monoclonal ascitic fluid

| Monoclonal antibody | Quantity of IgG/IgA from 1 ml of ascitic fluid (mg/ml-1) |
|---|---|
| P4C11 | 4.00 |
| P3E4 | 4.40 |
| *P2D3 | 1.14 |
| P2H6 | 2.40 |
| P2H9 | 0.90 |
| P2C6 | 3.00 |
| *M4F5 | 1.00 |
| **M4H2 | 1.70 |
| *M3A10 | 2.00 |

*Denotes three-way cross
**Initially found to be a three-way cross but was later found to be unstable and changed to a MAM-specific clone, see below.

The intensity of the monoclonal band staining in SPE showed strong positive correlation to the protein concentration results in Table 7. For example P4C11 showed a very darkly stained band in SPE and had a high protein concentration whilst P2H9 showed a faintly stained band and had a low protein concentration.

General Discussion

The results of HBsAg detection assays have confirmed that as a result of mutations, HBsAg in serum may not be detected by some monoclonal antibody based systems. Such mutations may cause the failure of either the capture antibody or the conjugated detection antibody to bind. These results show the importance of testing for a second marker in suspected cases of HBV infections when the initial screening test for HBsAg is negative. Both NP and MAM would have shown an anti-HBc only profile if tested for HBsAg with a monoclonal-based assay. The presence of HBsAg in the samples was revealed on testing by polyclonal based systems.

A mutation at amino acid 145 (glycine to lysine) was detected in patient MAM. Although this mutation was different from that previously described in vaccine escape mutants (glycine to arginine), the amino acid substitution was such that the predicted effect on the antigen structure is similar.

Patient NP did not have a mutation at codon 145 but multiple mutations as with patient MAM. Which of the mutations is responsible for the loss of detectability has not been determined. Interestingly in patient MAM the nucleotide sequences did not vary with change in HBsAg specificity in the HBsAg detection assays. This may have been due to the emergence of wild type virus present at less than 15-20% of the total viral load, the limit of detection by direct sequence analysis.

The production of monoclonal antibodies against the mutant hepatitis B surface antigens was successful. The number of clones produced in the NP and initial MAM fusion and the relative distribution of the specificities of the resulting antibodies were favourable. In order to identify anti-HBs secreting hybridomas, a sensitive but quick screening assay was required. An IgG reverse capture radioimmunoassay was chosen. The assay, though simple to set up, is capable of a very low background and a large dynamic range. The relative binding by positive clones of the labelled wild type and mutant HBsAg were unambiguously high and consistent giving reliable results.

Screening the hybridomas was initially carried out testing those clones derived from the MAM fusion with $^{125}$I MAM HBsAg and the NP clones with $^{125}$I NP HBsAg. Results of this assay gave an indication of those clones specifically producing anti-HBs which were recognising and thus binding to the MAM HBsAg or the NP HBsAg. All clones produced as a result of the two fusions were then tested with $^{125}$I WT HBsAg. No single clone gave a positive reaction to the WT HBsAg only. Either MAM/WT crosses or NP/WT crosses were found.

It was therefore possible to identify those clones which were recognising the MAM HBsAg or the NP HBsAg. Those clones which were also binding to the NP and WT HBsAg were also identified. To test for any cross reactivity between the hybridomas the clones produced from the MAM fusion were tested with the $^{125}$I NP HBsAg and vice versa. As a result of the screening assays, it was possible to categorize the clones as is listed in the Results section.

Positive controls included in the assay were two known WT HBsAg monoclonal antibodies, H3F5 and D2H5 whilst negative controls were PBS and 3D3F2, an anti-HIV gag monoclonal. As expected when used in the $^{125}$I WT HBsAg RIA, both H3F5 and D2H5 gave strong positive results. However when tested against $^{125}$I MAM HBsAg only H3F5 gave a positive reading and was negative when tested with $^{125}$I NP HBsAg. D2H5 though produced a positive signal with $^{125}$I NP HBsAg but was very weak when tested against $^{125}$I MAM HBsAg. Mutations in the MAM HBsAg eliminated the epitope for D2H5 whilst those in the NP HBsAg eliminated the H3F5 epitope.

The results obtained on testing with the SP and SZ mutant HBsAg show that the three-way cross antibodies are capable of detecting other mutant forms of HBsAg in addition to those used in the screening process. This confirms that the antibodies are binding to an epitope that is conserved between the wild type protein and mutant forms, and thereby confirms the value of including such antibodies in an HBsAg assay.

Although some of the hybridomas from the MAM fusions proved to be unstable, successful three-way crosses were obtained readily from both the MAM and NP fusions. Mutant forms of HBsAg other than the MAM and NP forms may be used for raising and/or for screening monoclonal antibodies according to the protocols described above.

Note: FIG. 1b is a typescript version of FIG. 1a. In the case of any discrepancy between FIG. 1a and FIG. 1b, FIG. 1a shall be taken as the authentic version.

Reagents

| Complete Medium | | Incomplete Medium |
|---|---|---|
| RPMI supplemented with | | RPMA supplemented with 5 mM Hepes buffer 2 nM L-glutamine |
| 5 mM | Hepes buffer | |
| 2 Mm | L-glutamine | |
| 0.05 M | 2-Mercaptoethanol | |
| 20% v/v | fetal calf serum | |
| 25 µg/ml$^{-1}$ | Fungizone | |
| 102 units ml$^{-1}$ | Penicillin | |
| 100 µg ml$^{-1}$ | Streptomycin | |
| HAT medium | | HT medium |
| Complete medium plus 5 × 10$^{-5}$ M hypoxanthine 2 × 10$^{-3}$ M aminopterin 8 × 10$^{-4}$ M thymidine | | Complete medium plus 5 × 10$^{-3}$ hypoxanthine 8 × 10$^{-4}$ thymidine |

0.02M Tris buffer DH7.6 (Tris buffer)

| | |
|---|---|
| Sodium azide | 1.00 g |
| Tris (hydroxymethyl) methylamine | 2.42 g |
| Distilled water | 900 ml |

Adjust pH to 7.6 with concentrated HCl and make that buffer up to 1 liter.

0.02M Tris BSA Buffer

Add 0.5% BSA to 0.02M Tris buffer pH7.6.

0.2M Phosphate Buffer (PB)

Solution A=0.2M KH$_2$PO$_4$

Solution B=0.2M Na$_2$HPO$_4$

Take 200 ml solution B. Adjust pH to 8.0 with solution A.

10, 20, 30 and 60 mM PB

For 10 mM PB dilute 0.2M PB 1:20 in distilled water

For 30 mM PB dilute 0.2M PB 1:6.6 in distilled water

For 60 mM PB dilute 0.2M PB 1:3.3 in distilled water

REFERENCES

CAMERON, C. H., COMBRIDGE, B. S., HOWELL, D. R., BARBARA, J. A. J. (1980). A sensitive immunoradiometric assay for the detection of hepatitis B surface antigen. J. Virol. Meth. 1: 311-323.

CARMEN, W. F., McINTYRE, G., KLEIN, H. (1992). Mutation of HBsAg in homograft recipients receiving hyperimmune globulin. J. Hepatology. 16: 59

CARMEN, W. F., WALLACE, L., KORULA, J., MacPHEE, R., DECKER, R. (1993). Natural occurrence of arginine at amino acid 145 of HBsAg undetected by current assays, causing fulminant hepatitis (abstract). Abstracts of the 1993 International Symposium on Viral Hepatitis and Liver Disease. Tokyo 10-14 May, p 289.

HARRISON, T. J., HOPES, E. A., YI, Z., KEOW, L. G. OON, C. J., ZUCKERMAN, A. J. (1993). Mutations in hepatitis B virus in carriers with co-existent surface antigen and antibody (abstract). Abstracts of the 1993 International Symposium on Viral Hepatitis and Liver Disease. Tokyo 10-14 May p:124.

HOWARD, C. R. KARTHIGESU, V., ALLISON, F., FORTUIN, M., WHITTLE, H. (1993). Hepatitis B virus variants with altered a determinants causing infections in immunised children (abstract). Abstracts of the 1993 International Symposium on Viral Hepatitis and Liver Disease. Tokyo 10-14 May p:75.

HAWKINS, A. E., GILSON, R. J. C., BEATH, S. V., BOXALL, E. H., KELLY, D. A., TEDDER, R. S., WELLER, I. V. D. (1994). Novel application of a point mutation assay: Evidence for transmission of hepatitis B viruses with pre-core mutations and their detection in infants with fulminant hepatitis B. J. Med. Virol 44:13-21.

KEARNEY, J. F., RADBRUCH, A., LIESEGANG, B., RAJEWSK, K. (1979). A new mouse myeloma cell line that has lost immuno-globulin expression but permits the construction of antibody-secreting hybrid cell lines. J. Immunol. 123: 439-450.

KEMENY D. M. & CHALLACOMBE S. J. (Eds). ELISA and Other Solid Phase Immunoassays, Theoretical and Practical Aspects. John Wiley, 1988.

KOHLER & MILSTEIN (1975) Nature 256:494

McMAHON, G., ERLICH, P. H., MOUSTAFA, Z. A., McCARTHY, L. A. DOTTAVIO, D., TOLPIN, M. D., NALDER, P. I., OSTBERG, L. (1992). Genetic alterations in the gene encoding the major HBsAg DNA and immunological analysis of recurrent HBsAg derived from monoclonal antibody-treated liver transplant patients. Hepatology. 15: 757

OKAOMOTO, H., YONO, N., NAZAKI, Y. (1992). Mutations within the S gene of hepatitis B virus transmitted from mothers to babies immunised with hepatitis B immune globulin and vaccine. Pediat. Res. 32: 264.

PUGH, J. et al. (1986) J. Med. Virol. 20:229-246

SALACINSKI, P, HOPE, J, McCLEAN, J, CLEMENT-JONES, C, SYKES, J., PRICE, J., LOWRY, P. J. (1979). A new simple method which allows theoretical incorporation of radioiodine into proteins and peptides without damage. J. Endocrinol. 81: 131-137.

TSU, T. T. & HERZENBERG, L. A. (1980) Solid Phase Radioimmunoassay In "Selected Methods In Cellular Immunology; Mishell, B. B. & Shiigi, S. M. Eds. pages 373-397. Freeman, San Francisco.

VALENZUELA et al. Nature 280:815 (1979)

The invention claimed is:

1. A monoclonal antibody which binds to an epitope of two or more HBsAg variants, wherein said epitope comprises the mutations selected from the group consisting of:
   (a) Met to Ile at amino acid 133, Phe to His at amino acid 134, and Asp to Val at amino acid 144 of NP HBsAg;
   (b) Met to Ile at amino acid 133, Phe to Asn at amino acid 134, Pro to Ser at amino acid 142, Ser to Leu at amino acid 143, and Gly to Lys at amino acid 145 of MAM HBsAg; and
   (c) Ser to Met at amino acid 143 of SP HBsAg.

2. A monoclonal antibody as claimed in claim 1 that is an IgG, IgM or IgA immunoglobulin.

3. Monoclonal antibody P2D3 as produced by the hybridoma designated P2D3 and deposited at the ECACC under accession number ECACC 97042331.

4. Monoclonal antibody M3A10 as produced by the hybridoma designated M3A10 and deposited at the ECACC under accession number ECACC 97042330.

5. Monoclonal antibody M4F5 as produced by the hybridoma designated M4F5 and deposited at the ECACC under accession number ECACC 97042519.

6. A monoclonal antibody as claimed in claim 1, in a humanized form.

* * * * *

UNITED STATES PATENT AND TRADEMARK OFFICE
CERTIFICATE OF CORRECTION

PATENT NO. : 7,393,933 B1
APPLICATION NO. : 09/402282
DATED : July 1, 2008
INVENTOR(S) : Richard Seton Tedder et al.

It is certified that error appears in the above-identified patent and that said Letters Patent is hereby corrected as shown below:

Column 5, Lines 49 and 50, "antibodies, which comprises an "internal image"" to read as --antibodies, which comprise an "internal image"--

Column 6, Lines 59 and 60, "may also comprises one or more" to read as --may also comprise one or more--

Column 13, Line 6, "5 mls" to read as --5 ml--

Column 16, Line 15, "Results of the methods is shown" to read as --Results of the methods are shown--

Column 17, Line 1, "Approximately a week after the fusion all wells" to read as --Approximately a week after the fusion, all wells--

Column 20, Line 15, "a previously pristane primed Balb/c mouse" to read as --a previously pristine primed Balb/c mouse--

Column 23, Line 56, "This varied between ascitic fluid which had been" to read as --This varied between ascitic fluids which had been--

Column 26, Line 7, "Mm" to read as --mM--

Signed and Sealed this

Twenty-second Day of June, 2010

David J. Kappos
*Director of the United States Patent and Trademark Office*

SEQUENCE LISTING

```
<160> NUMBER OF SEQ ID NOS: 10

<210> SEQ ID NO 1
<211> LENGTH: 56
<212> TYPE: PRT
<213> ORGANISM: Artificial Sequence
<220> FEATURE:
<221> NAME/KEY: VARIANT
<222> LOCATION: (23)...(23)
<223> OTHER INFORMATION: Xaa = Thr or Asn at position 23, Hepatitis B
      Virus

<400> SEQUENCE: 1

Leu Leu Pro Gly Ser Ser Thr Thr Ser Thr Gly Pro Cys Gln Thr Cys
 1               5                  10                  15

Thr Ile Thr Ala Gln Gly Xaa Ser Met Phe Pro Ser Cys Cys Cys Thr
            20                  25                  30

Lys Pro Ser Asp Gly Asn Cys Thr Cys Ile Pro Ile Pro Ser Ser Trp
        35                  40                  45

Ala Phe Ala Arg Phe Leu Trp Leu
    50                  55

<210> SEQ ID NO 2
<211> LENGTH: 56
<212> TYPE: PRT
<213> ORGANISM: Hepatitis B Virus

<400> SEQUENCE: 2

Leu Leu Pro Gly Ser Ser Thr Ser Thr Gly Pro Cys Arg Thr Cys
 1               5                  10                  15

Thr Thr Pro Ala Gln Gly Ile Ser Met Phe Pro Ser Cys Cys Cys Thr
            20                  25                  30

Lys Pro Ser Asp Gly Asn Cys Thr Cys Ile Pro Ile Pro Ser Ser Trp
        35                  40                  45

Ala Phe Gly Lys Phe Leu Trp Leu
    50                  55
```

<210> SEQ ID NO 3
<211> LENGTH: 168
<212> TYPE: DNA
<213> ORGANISM: Hepatitis B Virus

<400> SEQUENCE: 3
ctaattccag gatcatcaac caccagcacg ggaccctgca gaacctgcac gactcctgct    60
caaggaatct ctatgtatcc ctcctgttgc tgtacaaaac cttcggatgg aaactgcacc   120
tgtattccca tcccatcatc ctgggctttc ggaaaattcc tatgggag                168

<210> SEQ ID NO 4
<211> LENGTH: 168
<212> TYPE: DNA
<213> ORGANISM: Hepatitis B Virus

<400> SEQUENCE: 4
ctacttccag gaaccacaac aaccagtacg gggccatgcc agacctgcat gattactgct    60
caaggcaact ctaagtttcc ctcatgttgc tgtaccaaac ctacgacgg aaattgcact    120 tgtattccca tcccatgatc ctgggctttc gcaagatacc tatgggag                168

<210> SEQ ID NO 5
<211> LENGTH: 168
<212> TYPE: DNA
<213> ORGANISM: Hepatitis B Virus

<400> SEQUENCE: 5
ctaattccag gatcttcaac caccagtacg ggaccatgca aaacctgcac gactcctgct    60
caaggaacct ctacatatcc ctcctgttgc tgtacaaagt cttcggaaag aaattgcact   120
tgtattccca tcccatcatc ctgggctttc gcgaaattcc tatgggag                168

<210> SEQ ID NO 6
<211> LENGTH: 168
<212> TYPE: DNA
<213> ORGANISM: Hepatitis B Virus

<400> SEQUENCE: 6
ctaattccag gatcttcaaa caccagcacg ggactatgca gaacctgcac gattcctgct    60
caaggaacct ctatctatcc ctcctgttgc tgtaccaaac cttcgtctgg aaactgcacc   120
tgtattccca tcccaccatc ttgggctttc ggaaaattcc tatgggag                168

<210> SEQ ID NO 7
<211> LENGTH: 56
<212> TYPE: PRT
<213> ORGANISM: Hepatitis B Virus

<400> SEQUENCE: 7

Leu Leu Pro Gly Ser Ser Thr Thr Ser Thr Gly Pro Cys Arg Thr Cys
 1               5                  10                  15

Thr Thr Pro Ala Gln Gly Ile Ser Ile His Pro Ser Cys Cys Cys Thr
            20                  25                  30

Lys Pro Ser Val Gly Asn Cys Thr Cys Ile Pro Ile Pro Ser Ser Trp
        35                  40                  45

Ala Phe Gly Lys Phe Leu Trp Leu
    50                  55

<210> SEQ ID NO 8
<211> LENGTH: 56
<212> TYPE: PRT

```
<213> ORGANISM: Hepatitis B Virus

<400> SEQUENCE: 8

Leu Leu Pro Gly Ser Ser Thr Thr Ser Thr Gly Pro Cys Arg Thr Cys
 1               5                  10                  15

Thr Thr Pro Ala Gln Gly Ile Ser Ile Asn Pro Ser Cys Cys Cys Thr
                20                  25                  30

Lys Ser Leu Asp Lys Asn Cys Thr Cys Ile Pro Ile Pro Ser Ser Trp
            35                  40                  45

Ala Phe Gly Lys Phe Leu Trp Leu
        50                  55

<210> SEQ ID NO 9
<211> LENGTH: 56
<212> TYPE: PRT
<213> ORGANISM: Hepatitis B Virus

<400> SEQUENCE: 9

Leu Leu Pro Gly Ser Ser Thr Thr Ser Thr Gly Pro Cys Arg Thr Cys
 1               5                  10                  15

Thr Thr Pro Ala Gln Gly Ile Ser Met Phe Pro Ser Cys Cys Cys Thr
                20                  25                  30

Lys Pro Ser Asp Arg Asn Cys Thr Cys Ile Pro Ile Pro Ser Ser Trp
            35                  40                  45

Ala Phe Gly Lys Phe Leu Trp Leu
        50                  55

<210> SEQ ID NO 10
<211> LENGTH: 56
<212> TYPE: PRT
<213> ORGANISM: Hepatitis B Virus

<400> SEQUENCE: 10

Leu Leu Pro Gly Ser Ser Thr Thr Ser Thr Gly Pro Cys Arg Thr Cys
 1               5                  10                  15

Thr Thr Pro Ala Gln Gly Ile Ser Met Phe Pro Ser Cys Cys Cys Thr
                20                  25                  30

Lys Pro Met Asp Gly Asn Cys Thr Cys Ile Pro Ile Pro Ser Ser Trp
            35                  40                  45

Ala Phe Gly Lys Phe Leu Trp Leu
        50                  55
```